(12) United States Patent
Graham et al.

(10) Patent No.: US 7,090,490 B2
(45) Date of Patent: Aug. 15, 2006

(54) ATTACHABLE ORTHODONTIC HOOK SYSTEM

(76) Inventors: Brian Keith Graham, 5626 Crest De Ville, Orange, CA (US) 92667; Neil John Graham, 6017 Lido La., Long Beach, CA (US) 90803

( * ) Notice: Subject to any disclaimer, the term of this patent is extended or adjusted under 35 U.S.C. 154(b) by 139 days.

(21) Appl. No.: 10/732,527

(22) Filed: Jul. 26, 2004

(65) Prior Publication Data
US 2006/0019213 A1    Jan. 26, 2006

(51) Int. Cl.
*A61C 3/00* (2006.01)
(52) U.S. Cl. .......................................... 433/18; 433/19
(58) Field of Classification Search .................. 433/18, 433/19, 23, 24, 6
See application file for complete search history.

(56) References Cited

U.S. PATENT DOCUMENTS

| | | | |
|---|---|---|---|
| 6,293,790 B1 * | 9/2001 | Hilliard | 433/4 |
| 6,702,575 B1 * | 3/2004 | Hilliard | 433/6 |
| 2002/0192617 A1 * | 12/2002 | Phan et al. | 433/6 |
| 2003/0190575 A1 * | 10/2003 | Hilliard | 433/6 |
| 2003/0190576 A1 * | 10/2003 | Phan et al. | 433/6 |
| 2003/0198911 A1 * | 10/2003 | Knopp et al. | 433/6 |
| 2003/0198912 A1 * | 10/2003 | Mah | 433/6 |
| 2003/0207224 A1 * | 11/2003 | Lotte | 433/6 |
| 2004/0170941 A1 * | 9/2004 | Phan et al. | 433/6 |
| 2005/0130093 A1 * | 6/2005 | Lin | 433/18 |

* cited by examiner

*Primary Examiner*—Cary E. O'Connor
*Assistant Examiner*—Patrick J. Kilkenny
(74) *Attorney, Agent, or Firm*—Neil John Graham

(57) ABSTRACT

The invention involves an attachable orthodontic hook system for the attachment of an orthodontic hook to a vacuum formed orthodontic appliance, the hook designed for the reception of orthodontic elastics used to correct the patient's bite.

20 Claims, 4 Drawing Sheets ent Hook System

FIELD OF INVENTION

The invention involves an attachable hook system for the attachment of orthodontic elastics during orthodontic treatment. The hook is attached to a vacuum formed orthodontic removable orthodontic appliance constructed from a plastic or vinyl.

BACKGROUND OF THE INVENTION

Vacuum formed orthodontic appliances have been used for many years. Initially they were used for retention of teeth following orthodontic treatment and for bite plates. The appliance was subsequently used for a minor tooth movement, usually a single tooth. As time passed the appliance was used to align the anterior teeth wherein a mold of the teeth is made and the six anterior teeth are realigned and the appliance is constructed in the form of the desired position. The Invisalign Company came into being in 1998 wherein they used steriolithography to construct a series of vacuum formed appliances which moved the teeth progressively into a fully aligned position. At this point, generally, no attempt was made to move the patient's bite with the vacuum formed retainers. If elastics will move a bite in a fixed orthodontic appliance, why not in removable appliances? The use of elastics in removable vacuum formed appliance required elastic hooks which can be glued to the vacuum formed plastic appliances, but don't readily glue to vinyl appliances. The Raintree Essex Company markets tools which must be heated to make an elastic hook. The first tool makes a mushroom extrusion of material and the second tool defines the hook into a mushroom shape.

SUMMARY OF INVENTION

The invention involves an attachable orthodontic elastic hook system wherein an orthodontic hook is attached to a vacuum formed orthodontic appliance for the use of rubber bands to move the bite. A depression punch tool is used to depress the internal surface of the vacuum formed appliance and punch an insertion hole in the material. The orthodontic elastic hook is comprised of a hook and a pedestal base with a receiving post. The pedestal base fits into the recession and the receiving post passes through the punched hole to the exterior of the appliance. An elastic receiving hook is inserted over the receiving post and secured in place by a self-locking mechanism or screw type mechanism. In one embodiment the elastic hook is the shape of a mushroom, which is the typical shape of the lingual hook placed on a molar orthodontic band. In another embodiment the mushroom hook has a left and right circular hook, similar in size to the mushroom-shaped hook and mounted linearly in the same plane, which provides a larger hooking area, allowing the use of larger elastic bands. This embodiment requires the direction of the elastic hook to be rotationally stable. The rotational stability is provided by placing a rectangular hole in the retainer material and a pedestal base with a rectangular extension, which fits within the rectangular pedestal hole, and a female rectangular receptacle within the snap on hook for elastics.

DETAILED DESCRIPTION OF THE INVENTION

Figure 1:
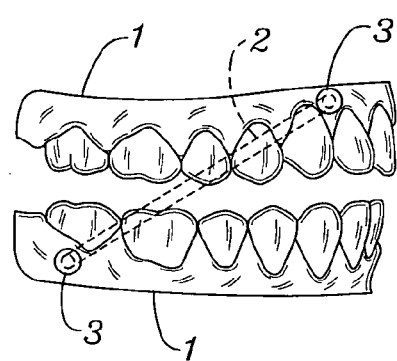
FIG. 1 is a side view of the removable hook on an appliance in a patient's mouth.
Figure 5:
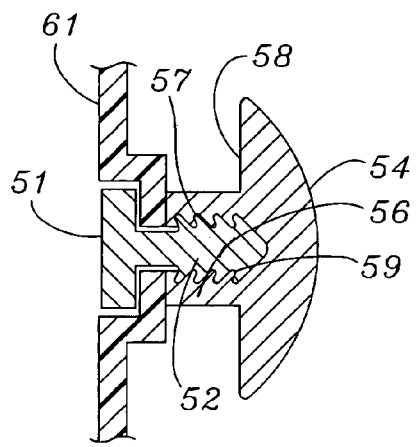
FIG. 5 is a sectional view of the hook with lock mounted to the appliance.
Figure 6:
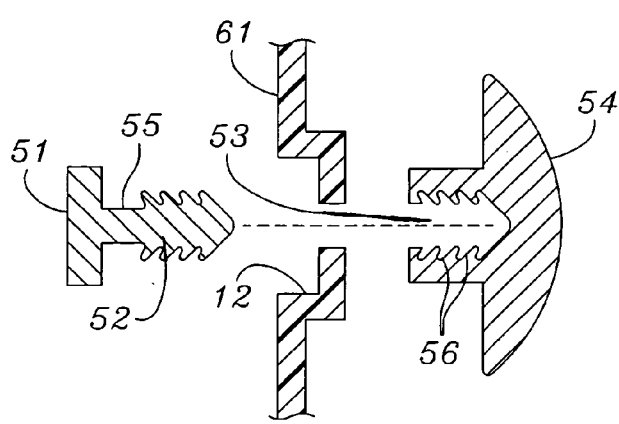
FIG. 6 is a disassembled view of the removable hook.
Figure 7:
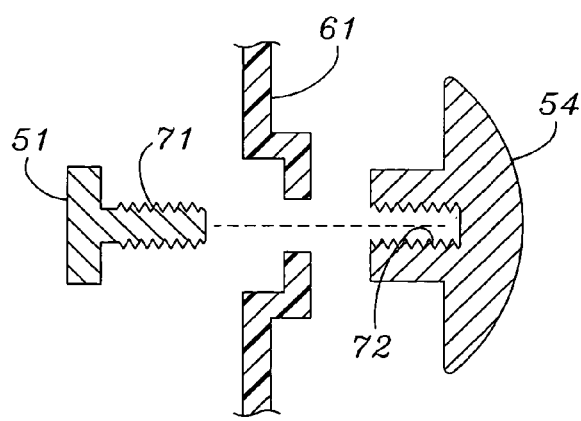
FIG. 7 is a perspective sectional view of the removable hook.
Figure 8:
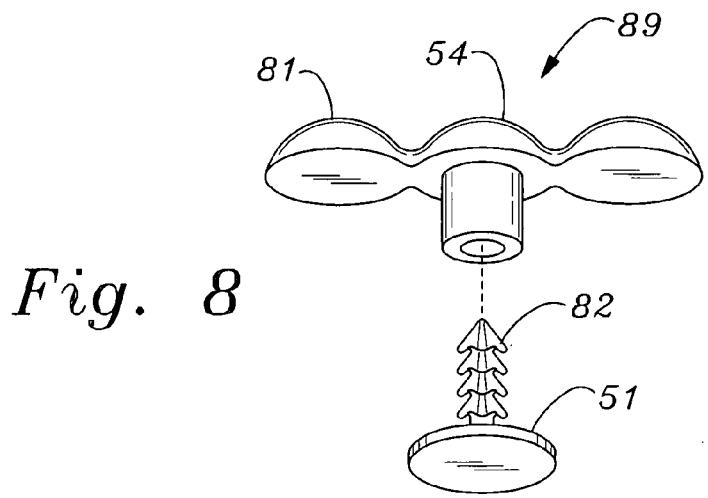
FIG. 8 is a side view of another embodiment of the hook.
Figure 9:
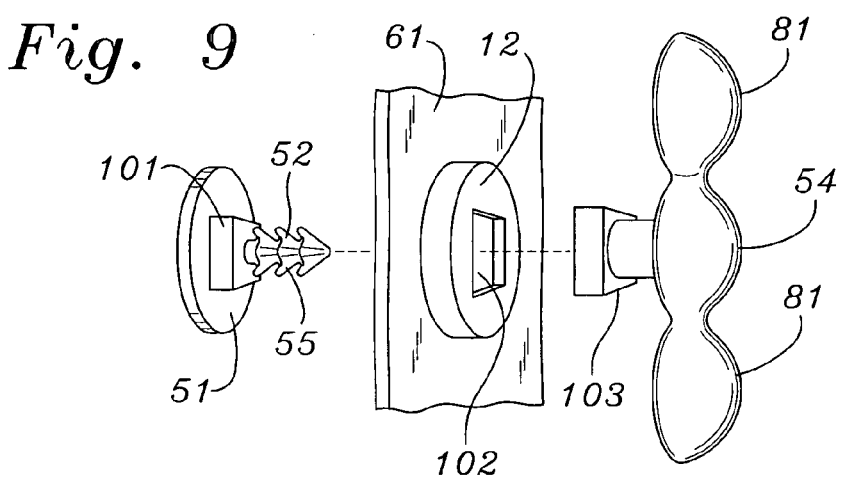
FIG. 9 is a view of the removable hook with a pedestal base.
Figure 10:
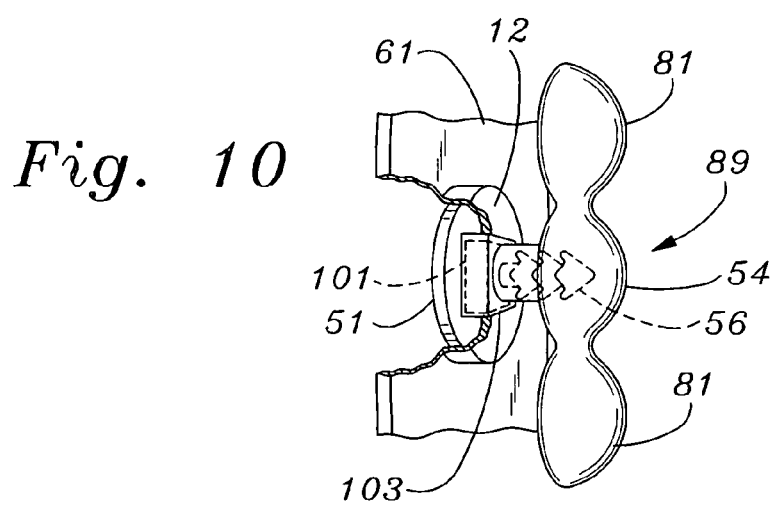
FIG. 10 is view of the removable hook in FIG. 9 with the hook mounted to the appliance.
Figure 11A:
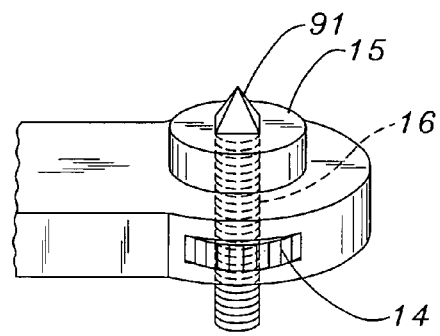
FIG. 11A is a side view of a jaw of the pliers.
Figure 11B:
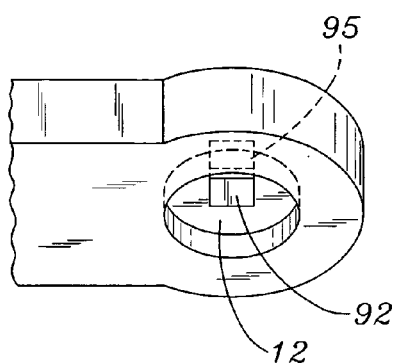
FIG. 11B is a side view of a jaw of the pliers.

The present invention is an attachable orthodontic hook system, wherein an attachable hook 3, FIG. 1, is attached to a vacuum formed orthodontic appliance 1. The hook 3 is used to attach rubber bands 2 used in orthodontic treatment. As shown in FIGS. 5, 6, and 7 the attachable hook 3 is comprised of a pedestal back 51, a locking longitudinal shaft 52, and a single button hook 54 or a button hook 54 with accessory hooks 81 as shown in FIGS. 8, 9, and 10.

Figure 2:
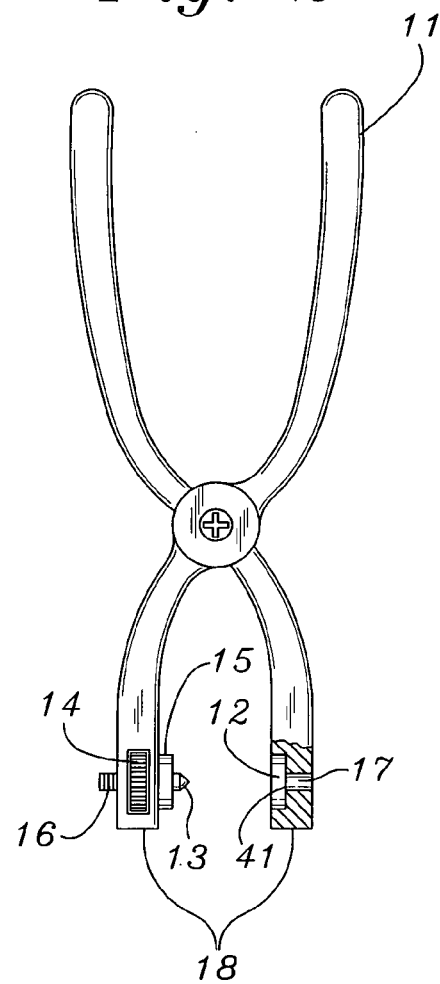
FIG. 2 is a side view of the countersink-punch pliers.
Figure 3:
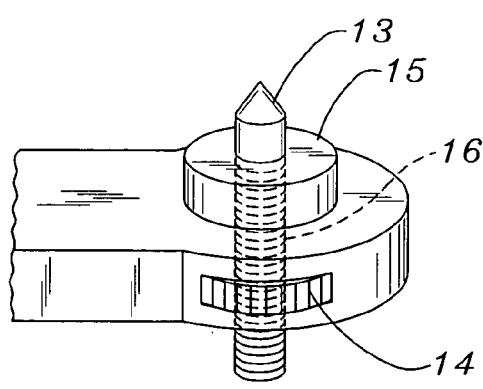
FIG. 3 is a perspective view of a jaw of the pliers.
Figure 4:
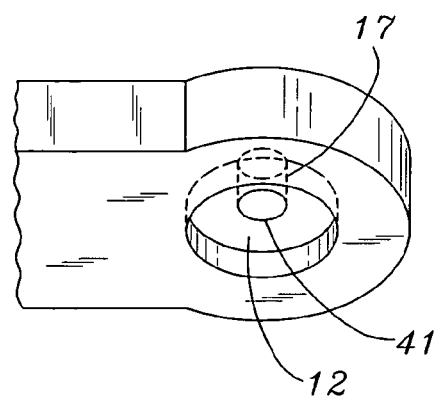
FIG. 4 is a perspective view of a jaw of the pliers.

The orthodontic vacuum formed appliance 1 is prepared for the placement of the attachable hook 3 by using a pair of countersink punch pliers 11 as in FIGS. 2, 3, and 4. The countersink punch pliers 11, are comprised of opposing jaws 18, one with a male countersink 15 which fits into a female countersink 12 in the opposing jaw. When the retainer material 1 is pressed between the opposing jaws 18 a countersink 12 is produced, as in FIGS. 5, 6, 7, 9, and 10, which allows a seat for the pedestal back 51 as shown in FIGS. 5, 6, 7, 9, and 10. In FIGS. 2 and 3 a hole producing punch 13 extends from the center of the surface of the male portion 15 extending towards the countersink 12 wherein the punch 13 fits into a cutting hole 41 and cuts a hole in the retainer material I in the center of the countersink 12. The cutting hole 41 is continued in the form of an escape channel 17, as shown FIGS. 2 and 4, allowing the cut material to escape. In FIG. 3 the punch 13 is the head of a threaded portion 16, which is mounted in a smooth channel in the jaw 18, wherein an adjustment set screw 14 is threaded and mounted to the threaded portion 16 allowing adjustment of the punch 13 by rotating the set screw 14.

In FIGS. 5 and 6, in a preferred embodiment, a circular locking shaft 52 is mounted centrally at a right angle to the pedestal back 51 wherein the locking shaft 52 contains locking extensions, or notches 57, directed towards the pedestal back 51. In FIGS. 5, 6, and 7 a button hook 54 in the shape of a half sphere comprises a female locking extension 56 extending at a right angle from the flat surface 58 of the half sphere 54. Contained within the female locking extension 56 is a longitudinal locking cavity 53 sized to fit over the locking shaft 52. The locking cavity 53 contains locking extensions 72 directed towards the button hook 54 wherein, in FIG. 6, the female locking extension 56 is placed over the locking shaft 52 firmly locking the orthodontic hook in place. FIG. 5 shows the attachable hook 3 attached to the appliance material 61. The appliance material 61 has been prepared to receive the pedestal back 51 with the attached locking shaft 52. In FIGS. 5, 6, 7, 9, and 10 the countersink 12 with the center hole 102 has been formed in the retainer material 61 by using the countersink punch plier 11 as shown in FIGS. 2, 3, 4, 11A, 11B, 12A, and 12B the countersink 12 is of sufficient depth to allow for the thickness of the retainer material 61 wherein the installed pedestal back 51 fits flush and does not protrude upon the patient's teeth or gums. The locking shaft 52 is inserted through the central 102 in the countersink 12 until the pedestal back 51 is seated in the countersink 12. The locking cavity 53 of the button hook 54 is placed over the horizontal locking shaft 52 as far as it will go. The female locking extensions 56 of the locking cavity 53 engage the notches or locking extensions, as shown in FIG. 5, and the button hook 57 is now firmly attached to the retainer 1.

FIG. 7 shows another preferred embodiment of the attachable hook 1 wherein the pedestal back 51 contains a threaded post 71 to fit the internal female thread 72 of the button hook 54. The button hook 54 is threaded on until tight. The pedestal back 51 may also contain an alien wrench fitting allowing the pedestal back 51 to be screwed on with an alien wrench.

FIG. 8 shows another embodiment the button hook 54. The hook is a tri-button hook 89 which contains accessory buttons 81 attached to the button hook 54 opposite to each other and on the same plane as the button hook 54. The advantage of the tri-button hook 89 is allowing easier attachment of orthodontic elastic bands 2 and an attachment which is more resistant to dislodging of the elastic bands 2.

Figure 12A:
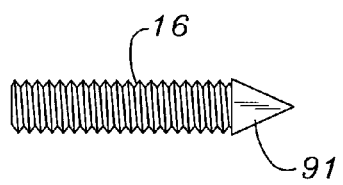
FIG. 12A is a view of the threaded hole punch.
Figure 12B:
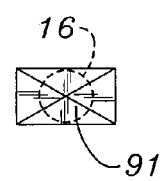
FIG. 12B is a cutting end view of the hole punch in FIG. 12A.

In a preferred embodiment the tri-button hook 89 is not allowed to rotate when mounted to the retainer 1. The stability is accomplished, as shown in FIGS. 9 and 10, by a rectangular interlock 101 on the pedestal back 51 which is integral with the locking shaft 52. A rectangular hole 102 is prepared in the center of the countersink 12 to fit over the rectangular interlock 101 and 103. The rectangular interlock 101 and 103 is of sufficient height that it extends beyond the retainer material 61. The pedestal back is inserted in the rectangular hole 102 allowing the female rectangular lock 101 and 103, mounted to the end of a female longitudinal shaft 56, to fit over the rectangular male interlock 101, preventing rotation of the tri-button hook 89. The rectangular hole 102 is cut with another embodiment of the countersink punch pliers 11 as shown in FIGS. 2, 3, 4, 11A, 11B, 12A, and 12B wherein the cutter 91, FIG. 9, is rectangular and the cutting escape channel 95, FIG. 12B, is also rectangular.

Figure 13:
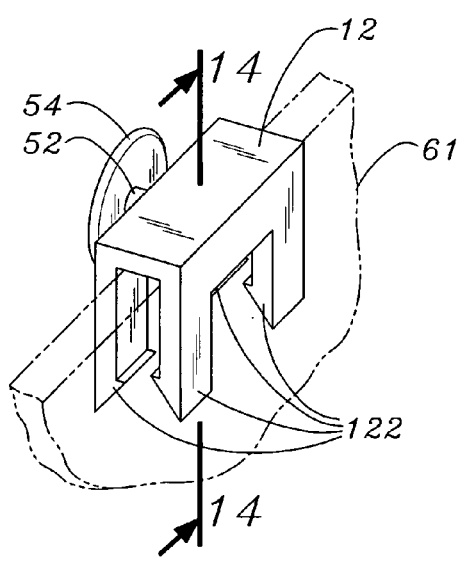
FIG. 13 is a perspective view of a clip mount.
Figure 14:
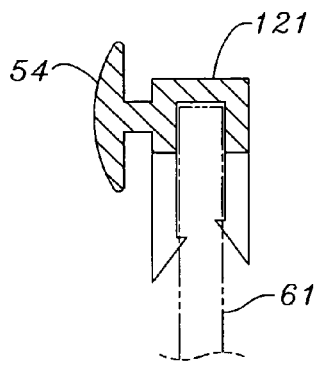
FIG. 14 is a cross-sectional view of the clip mount.

In another embodiment, in FIGS. 13 and 14, a clip 121 with locks 122 is fastened over the edge of the orthodontic material 61. The locking shaft 52 projects vertically from the clip 121, wherein a hook such as a button hook 54 is attached.

The attachable hook 3 may be constructed from plastic, vinyl, nylon, and metal. Other materials are possible. The intent of the invention is not limited to the preferred embodiments, but include embodiments wherein an elastic hook is attachable to a vacuum formed appliance. The countersink punch plier could be replaced with a machine or a punch with a hammer and anvil.

What is claimed:

1. An attachable hook system for the attachment of a hook to a vacuum formed orthodontic appliance for the reception of elastic bands comprising:
    a pedestal base with first and second sides, each side with a center, and a periphery;
    a longitudinal shaft with first and second ends, the second end mounted perpendicularly to the center of the second side of the pedestal base; and
    a hook for attaching elastics used in orthodontic treatment, the hook having a first flat side, a second curved side, and a periphery, the first flat side having perpendicularly mounted hollow longitudinal shaft sized to fit over the second end of the longitudinal shaft whereby the hook is attached to the vacuum formed orthodontic appliance by placing the pedestal base with the longitudinal shaft on the tooth side of the retainer and passing the longitudinal shaft through the vacuum formed appliance and attaching the hook by placing the hollow longitudinal shaft over the longitudinal shaft until firmly seated, thus locking the attachable hook to the orthodontic appliance, allowing attachment of elastic bands used during orthodontic movement of the bite.

2. An attachable hook system as in claim 1 wherein the longitudinal shaft has locking means, such as tiny projections or notches directed towards the second longitudinal shaft end, used for locking the hollow longitudinal tube when inserted over the longitudinal shaft.

3. An attachable hook system as in claim 1 wherein the hollow longitudinal shaft contains internal projections, or notches, facing the opposite direction of the longitudinal shaft locks whereby when the hollow longitudinal shaft is placed over the longitudinal shaft the shafts are held together locking the attachable elastic hook to the appliance.

4. An attachable hook system as in claim 1 wherein the hook for attaching elastics is a button hook the shape of a half sphere with an opposing flat surface, the hollow longitudinal shaft is attached perpendicularly mounted to the center of the flat surface.

5. An attachable hook system as in claim 1 wherein the hook for attaching elastics is three connected half spheres each with an opposing flat surface, the half spheres mounted in a row with the flat surfaces on the same plane and a hollow longitudinal shaft mounted perpendicularly to the flat surface of the middle half sphere.

6. An attachable hook system as in claim 1 wherein the pedestal base second side has a rectangular elevation for interlocking with the retainer material when the attachable hook is mounted to the vacuum formed retainer, preventing rotation of the mounted attachable hook.

7. An attachable hook system as in claim 1 wherein a tool means for recessing and punching a hole to the retainer material is used wherein the tool punches a round or rectangular hole to receive the pedestal base with locking shaft, and the tooth side of the retainer material is recessed a sufficient amount to allow the pedestal base to fit flush with the inner retainer material surface, preventing impingement of the pedestal base upon the patient's teeth or gums when the patient wears the appliance.

8. An attachable hook system as in claim 1 wherein the pedestal base is a tapered head of a flat headed screw and is connected to a threaded longitudinal shaft screwed onto a threaded hollow shaft which is attached to a hook, the screw may be a Phillips fitting or Hex wrench fitting.

9. An attachable hook system as in claim 1 wherein the pedestal base is a clip with parallel first and second sides joined at one end wherein each side contains inwardly directed locks, the second side containing a perpendicularly mounted horizontal shaft, the clip is placed over the edge of the appliance with the first side facing the patient's teeth and the second side facing the patient's cheek, the clip being locked in place using pliers.

10. An attachable hook system for the attachment of a hook to a vacuum formed orthodontic appliance for the attachment of elastic bands comprising:
- a pedestal base with first and second sides, each side with a center, and a periphery;
- a longitudinal shaft with first and second ends, the second end mounted perpendicularly to the center of the second side of the pedestal base;
- a hook for attaching elastics used in orthodontic treatment, the hook having a first flat side, a second curved side, and a periphery, the first flat side having a perpendicularly mounted hollow longitudinal shaft sized to fit over the second end of the longitudinal shaft whereby the hook is attached to vacuum formed orthodontic appliance by placing the pedestal base with a longitudinal shaft on the tooth side of the retainer and passing the longitudinal shaft through the vacuum formed appliance and attaching the hook by placing the hollow longitudinal shaft over the longitudinal shaft until firmly seated, thus locking the attachable hook to the orthodontic appliance, allowing attachment of elastic bands used during orthodontic movement of the bite; and
- counter punch pliers for forming a recession in the vacuum formed appliance material and creating a hole in the recession sized to receive the pedestal base in a manner the pedestal base is flush with the inner appliance surface and the hole sized to receive the longitudinal shaft of the pedestal base.

11. An attachable hook system as in claim 10 wherein the longitudinal shaft has locking means, such as tiny projections or notches, directed towards the second longitudinal shaft end, used for locking the hollow longitudinal tube inserted over the longitudinal shaft.

12. An attachable hook system as in claim 10 wherein the hollow longitudinal shaft has locking means, such as tiny projections or notches, facing the opposite direction of the longitudinal shaft locks whereby when the hollow shaft is placed over the longitudinal shaft they are held together preventing removal.

13. An attachable hook system as in claim 10 wherein the hook for attaching elastics is a button hook the shape of a half sphere and a flat surface, the hollow longitudinal shaft is perpendicularly mounted to the center of the flat surface.

14. An attachable hook system as in claim 10 wherein the hook for attaching elastics is three connected half spheres each with a flat surface and a half sphere, the half spheres are mounted in a row with the flat surfaces on the same plane and a hollow longitudinal shaft mounted perpendicularly to the flat surface of the middle half sphere.

15. An attachable hook system as in claim 10 wherein the pedestal base second side has a rectangular elevation for interlocking with the retainer material when the attachable hook is mounted to the vacuum formed retainer, preventing rotation of the mounted attachable hook.

16. An attachable hook system as in claim 10 wherein a tool means for recessing and punching a hole to the retainer material is used, the tool punches a round or rectangular hole to receive the pedestal base with locking shaft, and the tooth side of the retainer material is recessed sufficient amount for the pedestal base to fit flush with the inner retainer surface, preventing impingement of the pedestal base upon the patient's teeth or gums when the patient wears the appliance.

17. An attachable hook system as in claim 10 wherein the pedestal base is a tapered head of a flat headed screw connected to a threaded longitudinal shaft screwed into a threaded hollow shaft which is attached to a hook, the screw may be a Phillips fitting or Hex wrench fitting.

18. An attachable hook system as in claim 10 wherein the pedestal base is a clip with parallel first and second sides joined at one end wherein each side contains inwardly directed locks, the second side containing a perpendicularly mounted horizontal shaft, the clip is placed over the edge of the appliance with the first side facing the patient's teeth and the second side facing the patient's cheek, the clip being locked in place using pliers.

19. An attachable hook system as in claim 10 wherein the countersink punch plier is comprised of:
- pliers with handles, a joint, and first and second jaws, each jaw having an inner and outer surface;
- an elevation on the inner surface of the first jaw forming a recess in the vacuum-formed material for receiving the pedestal base;
- a male portion of a hole cutting punch comprised of a threaded shaft with a cutting point projecting from the elevation;
- a female portion of the hole cutting punch on the inner surface of the second jaw which is aligned with the male portion when the jaws are closed;
- a channel extending from the female portion of a the hole punch to the outer surface of the second jaw, allowing escape of the cut appliance material; and
- a threaded adjustment screw in the first jaw fitted to the threaded shaft of the male hole punch wherein the rotation of the threaded adjustable screw adjusts the projection of the male cutting head.

20. A process of attaching an elastics receiving hook to an orthodontic vacuum formed appliance comprising:
- recessing the appliance with a countersink punch plier wherein the countersink is sized to receive the elastic receiving hook comprised of a pedestal base, longitudinal locking shaft, and hollow longitudinal locking shaft with an elastic receiving hook;
- punching the appliance material with the countersink punch producing a hole to receive the longitudinal shaft of the elastic receiving hook;
- inserting the longitudinal shaft through the punched hole;
- seating the pedestal base in the recess; and
- placing the hollow longitudinal shaft slidably over the longitudinal shaft until fully seated.

* * * * *